US009314237B2

(12) United States Patent
Anspach, III et al.

(10) Patent No.: US 9,314,237 B2
(45) Date of Patent: Apr. 19, 2016

(54) KNOTLESS SUTURE ANCHOR AND RECEPTACLE COMBINATION

(75) Inventors: William E. Anspach, III, Stuart, FL (US); Eddy H. Del Rio, Royal Palm Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 732 days.

(21) Appl. No.: 12/154,090

(22) Filed: May 20, 2008

(65) Prior Publication Data

US 2009/0292313 A1 Nov. 26, 2009

(51) Int. Cl.
*A61B 17/04* (2006.01)
*A61B 17/86* (2006.01)
*A61B 19/00* (2006.01)

(52) U.S. Cl.
CPC ......... *A61B 17/0401* (2013.01); *A61B 17/0487* (2013.01); *A61B 17/864* (2013.01); *A61B 2017/044* (2013.01); *A61B 2017/0409* (2013.01); *A61B 2017/0414* (2013.01); *A61B 2017/0437* (2013.01); *A61B 2017/0445* (2013.01); *A61B 2017/0448* (2013.01); *A61B 2019/307* (2013.01)

(58) Field of Classification Search
CPC .. A61B 17/0401; A61B 17/864; A61B 17/86; A61B 17/8685; A61B 17/68; A61B 17/8625; A61B 2017/0445; A61B 2017/0448; A61B 2017/0422; A61B 2017/0424; A61B 2017/043; A61B 2017/0432; A61B 2017/0433; A61B 2017/0403
USPC ......... 606/232, 306, 310, 313, 319, 320, 301, 606/304, 307, 308; 623/13.14; 411/395
See application file for complete search history.

(56) References Cited

U.S. PATENT DOCUMENTS 4,738,255 A  4/1988 Goble et al.
4,750,492 A  6/1988 Jacobs
(Continued)

FOREIGN PATENT DOCUMENTS

WO  WO2007/147634  * 12/2007 ................ A61F 2/08

OTHER PUBLICATIONS

International Preliminary Report on Patentability, dated May 22, 2007, in International Application No. PCT/US2005/026091, 5 pages.

(Continued)

*Primary Examiner* — Christopher L Templeton
(74) *Attorney, Agent, or Firm* — Meunier Carlin & Curfman LLC

(57) ABSTRACT

A threaded receptacle for receiving a commercially available knotless suture anchor is designed to secure sutures for tying soft tissue in patients that have bone characteristics where the typical anchor is avulsed because of the weakness of the bone structure, a cavity exists in the bone where an anchor has been removed. The threaded receptacle includes a helical thread that is maximized to provide sustaining surface and includes a central bore and an internal flange that is dimensioned to provide a central opening to allow the knotless suture anchor to pass into a cavity and prevent the knotless suture anchor from being expulsed when deployed. The internal dimension of the cavity is designed to cause the tips of the wings of the anchor to fold to assure sufficient holding structure. In a second embodiment the reduced diameter portion is at the end of the receptacle so that the anchor passes through the end of the receptacle and the locking portion remains within the receptacle having both the receptacle and anchor serving as a means for securing the mechanism to the bone.

10 Claims, 8 Drawing Sheets

(56) References Cited

U.S. PATENT DOCUMENTS

| | | | |
|---|---|---|---|
| 5,013,316 A | 5/1991 | Goble et al. | |
| 5,100,417 A | 3/1992 | Cerier et al. | |
| 5,156,616 A * | 10/1992 | Meadows | A61B 17/0401 411/395 |
| 5,383,905 A | 1/1995 | Golds et al. | |
| 5,456,685 A * | 10/1995 | Huebner | 606/321 |
| 5,472,452 A | 12/1995 | Trott | |
| 5,492,442 A * | 2/1996 | Lasner | 411/426 |
| 5,571,139 A | 11/1996 | Jenkins, Jr. | 606/232 |
| 5,584,835 A * | 12/1996 | Greenfield | 606/232 |
| 5,645,589 A | 7/1997 | Li | |
| 5,690,649 A | 11/1997 | Li | |
| 5,702,397 A | 12/1997 | Goble et al. | |
| 5,725,541 A | 3/1998 | Anspach, III et al. | |
| 5,728,136 A | 3/1998 | Thal | |
| 5,741,300 A | 4/1998 | Li | |
| 5,766,250 A * | 6/1998 | Chervitz et al. | 606/232 |
| 5,814,071 A | 9/1998 | McDevitt et al. | |
| 5,843,087 A | 12/1998 | Jensen et al. | |
| 5,843,127 A | 12/1998 | Li | |
| 5,891,168 A | 4/1999 | Thal | |
| 5,902,321 A | 5/1999 | Caspari et al. | |
| 5,931,840 A * | 8/1999 | Goble et al. | 606/916 |
| 5,948,000 A | 9/1999 | Larsen et al. | |
| 5,948,001 A | 9/1999 | Larsen | |
| 5,957,953 A | 9/1999 | DiPoto et al. | |
| 5,968,044 A | 10/1999 | Nicholson et al. | |
| 6,022,373 A | 2/2000 | Li | |
| 6,045,574 A | 4/2000 | Thal | |
| 6,086,608 A | 7/2000 | Ek et al. | |
| 6,129,762 A | 10/2000 | Li | |
| 6,143,017 A | 11/2000 | Thal | |
| 6,149,669 A | 11/2000 | Li | |
| 6,156,039 A | 12/2000 | Thal | |
| 6,200,329 B1 | 3/2001 | Fung et al. | |
| 6,221,107 B1 | 4/2001 | Steiner et al. | |
| 6,231,606 B1 | 5/2001 | Graf et al. | |
| 6,290,711 B1 | 9/2001 | Caspari et al. | |
| 6,328,758 B1 | 12/2001 | Tornier et al. | |
| 6,524,317 B1 | 2/2003 | Ritchart et al. | |
| 6,524,328 B2 | 2/2003 | Levinson | |
| 6,527,794 B1 | 3/2003 | McDevitt et al. | |
| 6,569,188 B2 | 5/2003 | Grafton et al. | |
| 6,616,665 B2 | 9/2003 | Grafton et al. | |
| 6,660,008 B1 * | 12/2003 | Foerster et al. | 606/327 |
| 6,689,135 B2 | 2/2004 | Enayati | |
| 6,692,516 B2 | 2/2004 | West, Jr. et al. | |
| 6,730,092 B2 * | 5/2004 | Songer | A61B 17/0401 606/232 |
| 6,770,076 B2 | 8/2004 | Foerster | |
| 6,923,824 B2 | 8/2005 | Morgan et al. | |
| 7,090,690 B2 * | 8/2006 | Foerster | A61B 17/0401 606/232 |
| 7,144,413 B2 * | 12/2006 | Wilford et al. | 606/232 |
| 7,144,415 B2 | 12/2006 | Del Rio et al. | |
| 7,713,286 B2 | 5/2010 | Singhatat | |
| 2004/0133239 A1 | 7/2004 | Singhatat | |
| 2005/0177165 A1 * | 8/2005 | Zang et al. | 606/73 |
| 2006/0106422 A1 * | 5/2006 | Del Rio et al. | 606/232 |
| 2008/0275469 A1 | 11/2008 | Fanton et al. | |
| 2009/0281580 A1 * | 11/2009 | Emannuel | 606/304 |
| 2009/0292321 A1 * | 11/2009 | Collette | 606/303 |

OTHER PUBLICATIONS

Written Opinion, dated Mar. 6, 2006, in International Application No. PCT/US2005/026091, 4 pages.

International Search Report, dated Mar. 6, 2006, in International Application No. PCT/US2005/026091, 1 page.

* cited by examiner

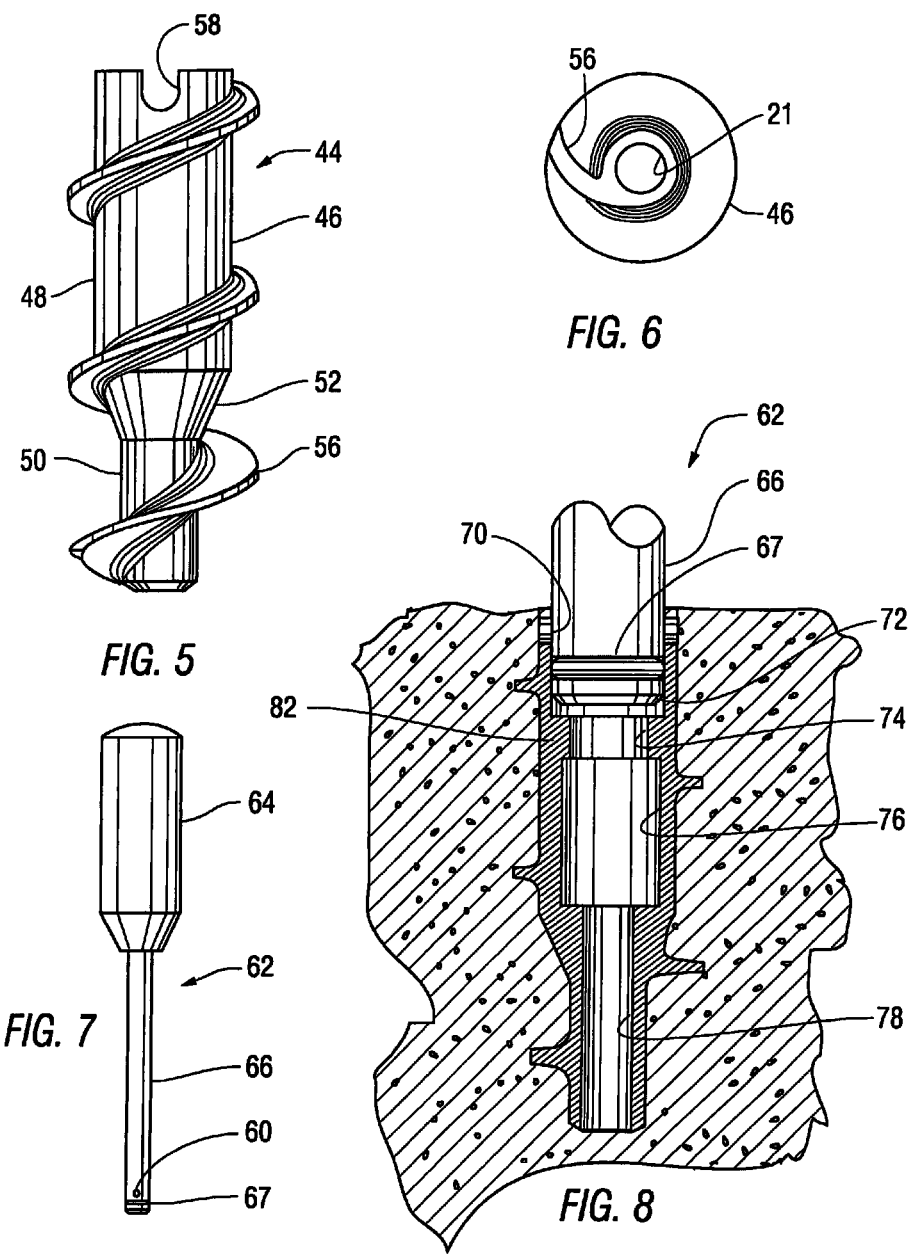

KNOTLESS SUTURE ANCHOR AND RECEPTACLE COMBINATION

RELATED APPLICATIONS

This invention relates to the anchor disclosed and claimed in U.S. Pat. No. 7,144,415 granted to the joint inventors of this patent application on Dec. 5, 2006, entitled ANCHOR/SUTURE USED FOR MEDICAL PROCEDURES and assigned to the same assignee as this patent application and is incorporated in its entirety by reference in this patent application.

FEDERALLY SPONSORED RESEARCH OR DEVELOPMENT

Not applicable

TECHNICAL FIELD

This invention relates to a knotless suture anchor and more particularly to the combination of this type of anchor and a receptacle for attaching soft tissue to the bone of a patient used in medical procedures.

BACKGROUND OF THE INVENTION

As is well known in the medical field, there is an increasingly occurring problem where connective tissue, such as tendons and ligaments, tear or detach from the associated bone. While this invention is not limited to the method of incisions used in this type of operation, there is a trend to use arthroscopic surgical techniques rather than cutting large incisions in the tissue of the patient for performing the reattachment operation in this medical procedure. A typical problem that is the concern of this invention, although not the only one, is the tear or detachment of the soft tissue in rotator cuff as to where the supraspinatus tendon separates from the humerus. In this type of medical procedure the advent of the knotless suture has played an important roll in allowing the surgeon to perform this type of operation using arthroscopic techniques.

Unfortunately, the known knotless types of suture anchors that are capable of supporting the tendon to the bone is not efficacious for certain types of patients or where the surgeon inadvertently or aggressively removes the outer cortical layer of the bone while preparing the area of concern during the operative procedure or an anchor has been removed from the bone cavity and another anchor is intended to replace it. In these instances the bone structure is not sufficiently strong to hold the knotless suture types of anchors and under the circumstances the anchor or suture anchor will avulse from the bone. This failure mode is more common in the osteoporotic bone found in older patients. Obviously, the non screw-in types of anchors have a higher propensity to avulse from the bone than the screw type of anchor. That's because the knotless devices require the sutures to be placed through the soft tissue and threaded through the anchor prior to placement of the anchor into the bone. The knotless suture typically either have wings that expand inside the bone or have an asymmetrical shape that, under load, will toggle inside the bone such that it is captured below the bone surface. These anchors have less surface area in contact with the bone than do the screw type of anchor, so that suture anchors avulsion from the bone is more likely to occur.

The medical industry has seen a number of devices that have attempted to solve the problem of prematurely avulsion of anchors from the bone. For example, U.S. Pat. No. 5,728, 136 granted to Thal on Mar. 17, 1998 entitled "KNOTLESS SUTURE ANCHOR ASSEMBLY" describes a knotless suture anchor that is in the form of a spike that is inserted in a ratcheting manner into a sleeve that was previously inserted into the cavity of the bone. The spike carrying the suture is inserted through the tissue being fastened to the bone before being attached to the anchoring sleeve.

U.S. Pat. No. 6,689,135 granted to Enayati on Feb. 10, 2004 entitled "EXPANDABLE BONE FASTENER AND INSTALLATION TOOL" describes a device similar to the Thal structure that includes a sleeve mounted in the bone cavity and a pin that is inserted into the sleeve. The pin includes barbs or wings that expand into slots formed in the sleeve and the suture is attached to the pin.

U.S. Pat. No. 5,472,452 granted to Trott on Dec. 5, 1995 entitled "RECTILINEAR ANCHOR FOR SOFT TISSUE FIXATION" relates to a rectangular shaped inner member having a wave-like outer surface that fits into a rectangular opening formed into a rectangular shaped outer member such that when the inner member is inserted into the opening it forces wing-like elements formed on the outer member that are forced into the bone for holding the same into the bone cavity.

U.S. Pat. No. 5,584,835 granted to Greenfield on Dec. 17, 1996 entitled "SOFT TISSUE TO BONE FIXATION DEVICE AND METHOD, is another system intended to secure an anchor to the bone to avoid avulsion and includes a threaded outer member that is tapped into the bone cavity and an inner member that is either rectangular or circular shaped in cross section.

U.S. Pat. No. 5,013,316 granted to Goble et al on May 7, 1991 entitled "SOFT TISSUE ANCHOR SYSTEM" which describes a footing stud that is drilled into the bone and includes self tapping threads. The footing stud includes a cylindrical recess that accommodates a tack that includes a shaft with wing-like elements much in the shape of an arrow head. The point is inserted through the soft tissue and into the recess and at the opposite end of the shaft is a broad head with protruding spikes that are impaled into the soft tissue.

U.S. Pat. Nos. 6,616,665 and 6,569,188 granted to Grafton et al on Sep. 9, 2003 entitled "METHOD OF ROTATOR CUFF REPAIR" and on May 27, 2003 entitled "HEX DRIVE BIOABSORBABLE TISSUE ANCHOR", respectively, disclose a headed bio-absorbable tissue anchor with a continuous thread spiraling around a tapering central core. A driver tool includes a distal end that fits into slots formed on the head for turning the threaded unit into the bone.

These referenced patents, which are incorporated herein by reference, describe the typical prior art devices of anchors that utilize sutures or flanges where the apparatus is designed so that the outer and inner components are specifically designed to mate with each other. Also shown in these prior art devices are anchors that are threaded to the bone and in some instances the anchors are of the knotless suture types. Hence, while it is fair to state that the prior art discloses anchors that are utilized to screw into the bone, these prior art types of devices are strictly anchors that are intended as a medical structure that is capable of being initially inserted into the bone for soft tissue attachment. None of these prior art devices are intended to solve the problem attendant from the occasion when the avulsion of a previously installed anchor from the bone of the patient occurs. As mentioned earlier, avulsion of the anchor from the bone typically occurs from osteoporotic bone found in older patients or where the surgeon aggressively removes the outer, cortical layer of the bone while preparing the area for soft tissue repair.

While the present invention utilizes the screw-in types of anchors that are described in the aforementioned patents, this feature of the invention is only utilized in the receptacle. This invention combines the effectiveness of these screw-in features with the convenience and efficaciousness of a knotless suture anchor. It is fair to state that this invention serves to obviate the avulsion problem and is different from the types of devices described in the above mentioned patents from both the structural design and the design philosophy as will become more apparent from the description to follow. Where the prior art devices are designed such that the inner and outer components are mutually dependent on each other, the present invention deviates from this philosophy and utilizes a commercially available knotless suture anchor that is susceptible to avulse from the bone under certain bone conditions and provides a receptacle that allows its use so as to obviate the avulsion problem. In accordance with this invention, the knotless suture anchor that is commercially available from The Anspach Effort, Inc. of Palm Beach Gardens, Fla., is an example of a commercially available anchor that is adapted to be utilized with the receptacle of this invention. It should be understood that other types of knotless suture anchors may also be utilized with this invention, as for example, the anchors available through Opus Medical, or Depuy Mitek and others. In accordance with this invention, two embodiments are presented and each of the embodiments utilizes the type of knotless suture described in U.S. Pat. No. 7,144,415, supra. In one embodiment, the receptacle includes outer threads that attach to the bone and the knotless anchor passes through a central bore and through the distal end where the suture anchor is deployed to impale the bone. In the second embodiment the knotless anchor is captured in a recess of the receptacle where the tips of the wings engage the inner surface of the central bore of the receptacle. With respect to the question of obviousness, it is noted that notwithstanding the fact that the tips of the wings of these commercially available anchors are relatively thin and fragile, they are intended to pierce or impale the bone structure and attach to the bone with sufficient strength to cinch the soft tissue to the bone by the suture attached thereto, it is hardly obvious to utilize these types of anchors where the wings are not utilized to impale the bone structure. Hence, according to one embodiment of the present invention the inner bore is necked down at the distal end that allows the winged portion of the anchor to pass therethrough while the locking portion is captured in the recess. Upon deployment, the wings are folded in half and each half moves toward each other in the shape of a "V" and impale the bone in the radial direction. In the second embodiment the impaling aspect of the anchor is not utilized to secure the anchor to the bone, but rather remain within the receptacle.

In this invention the receptacle for both embodiments includes outer threads that serve to tap the receptacle into the bone and includes a tool engaging portion that allows the surgeon to thread the screw-like receptacle into the bone. The receptacle includes a circular central recess opened at the proximate end for receiving the knotless suture anchor and an inner flange or projection that allows the wings of the anchor to pass there-through and prevent the anchor to retreat when the wings are deployed. In one embodiment, the diameter of the recess is such that the tip of each of the wings are forced to fold over itself that enhances the structural integrity of the unit so as to allow the surgeon to exert sufficient force to withdraw the suture in order to cinch the soft tissue to the bone while at the same time providing an anchor that obviates the avulsion problem. In the other embodiment, the wings are deployed and extend beyond the distal end of the central through bore of the bore and enter the bone to augment the holding force of the anchor/receptacle device. Obviously, this allows the surgeon to exercise his judgment as to which embodiment would be appropriate, namely whether to utilize the anchor without the receptacle or utilize the combined anchor/receptacle. This is in contrast to heretofore known systems where, if the receptacle cannot be utilized, the entire unit (the receptacle/anchor) is not usable.

SUMMARY OF THE INVENTION

An object of this invention is to provide an anchor/receptacle such that the anchor can be utilized with or without the receptacle.

A feature of one embodiment of this invention is to provide a receptacle with a cylindrical shaped main body having a helix thread around the outer periphery and a central bore having a reduced diameter portion at the distal end and capable of accepting a removable knotless suture anchor with a locking portion having a larger diameter than the diameter of the reduced portion so as to permit the winged portion of the anchor to pass there-through and when deployed being capable of impaling the bone of the patient where the knotless suture anchor is locked in place in the receptacle when deployed.

A feature of this invention is to provide a receptacle that utilizes a main body with a large diameter portion and a small diameter portion that carries a helical thread having the same outer diameter for both portions of the main body so as to enhance the holding surface area and in another embodiment the diameter of the main body is uniform.

A feature of another embodiment of this invention is that the receptacle is designed to accommodate a commercially available anchor and is dimensioned to accept the anchor in a central bore and when deployed, the wings become wider than a shoulder formed in the bore so as to prevent the anchor from dislodging from the receptacle.

Another feature of the of the anchor is where the wings of the anchor extend radially and its tips are folded over itself so as bear against the wall of the central bore thereby contributing to the structural integrity of the anchor and enhance its holding force.

The foregoing and other features of the present invention will become more apparent for description and accompanying drawings

BRIEF DESCRIPTION OF THE DRAWINGS

FIG. 5 is a view in elevation illustrating the receptacle of this invention:

FIG. 6 is a bottom plan view of the receptacle that is depicted in FIG. 5;

FIG. 7 is a side elevation view of the tool utilized to insert the screw depicted in FIG. 5 into the bone of a patient.

FIG. 8 is a fragmentary view partially in cross section illustrating an enlargement of the tool depicted in FIG. 5 and an enlargement showing of the distal end of the tool depicted in FIG. 7;

DETAILED DESCRIPTION OF THE INVENTION

While this invention is being described in its preferred embodiment as having a specific type of rivet or anchor utilized in the chamber of a receptacle, as would be appreciated by one skilled in this art, other types of anchors or variations thereof can be utilized without departing from this invention. However, in accordance with this invention, the specific anchor inserted in the receptacle is of the type that can be utilized with or without a receptacle.

Figure 1:
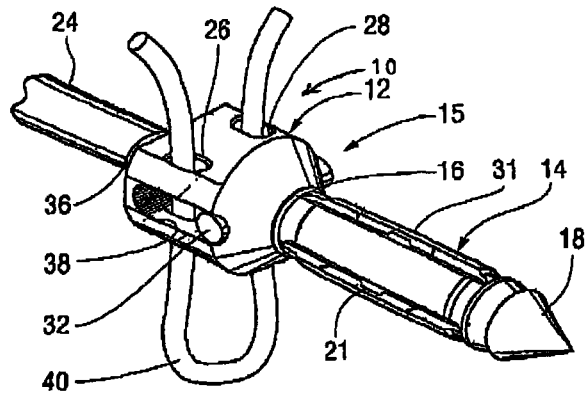
FIG. 1 is a view in prospective illustrating the prior art knotless anchor of the type that is commercially available from the assignee of this patent application.
Figure 2:
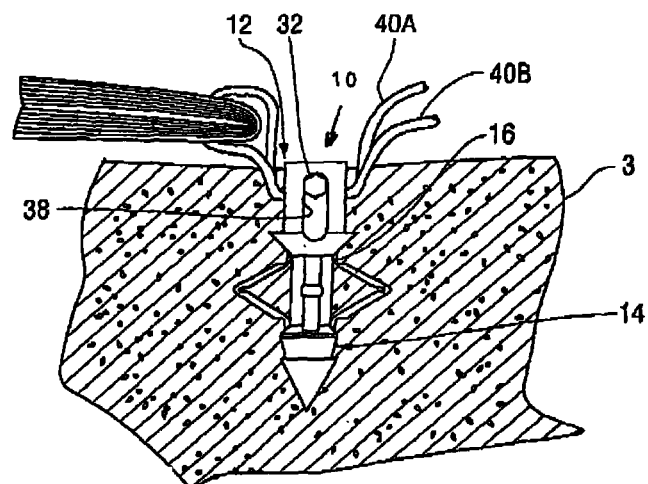
FIG. 2 is a schematic illustration of the prior art anchor depicted in FIG. 1 when attached to soft tissue and deployed in the bone structure.

Referring next to the prior art anchor of the type that is commercially available and described in U.S. Pat. No. 7,144,415, supra, as shown in FIGS. 1 through 4, the knotless suture anchor generally illustrated as reference numeral 10 includes a the suture locking mechanism generally illustrated by reference numeral 12 and the anchor generally illustrated as reference numeral 14. The anchor 14 includes a cylindrical proximate end 16 and a cylindrical distal end 18, axially spaced there from. A pointed end portion 20 projects axially from the distal end 18 and serves to impale the bone as it is driven by the insertion gun (not shown, but illustrated in the U.S. Pat. No. 7,144,415 patent, supra). The surgeon typically utilizes the gun to insert the anchor/suture locking mechanism to force the anchor into the bone as shown in FIG. 2 by virtue of the shaft 24 connected thereto. As one skilled in this art knows, at times the surgeon will use a mallet to tap the end of the gun to make certain the anchor is fully inserted into the cavity of the bone. After the anchor is inserted, the surgeon then squeezes the gun trigger so as to withdraw the shaft 24. The shaft being attached to the anchor drives the tip upwardly which is in a direction opposing the force used to insert the anchor and hence cause the wings 31 (four equally spaced around the circumference of the anchor) to collapse and be forced radially outwardly and defines a "V" shape and impales into the soft structural portion of the bone.

Figures 3, 4:
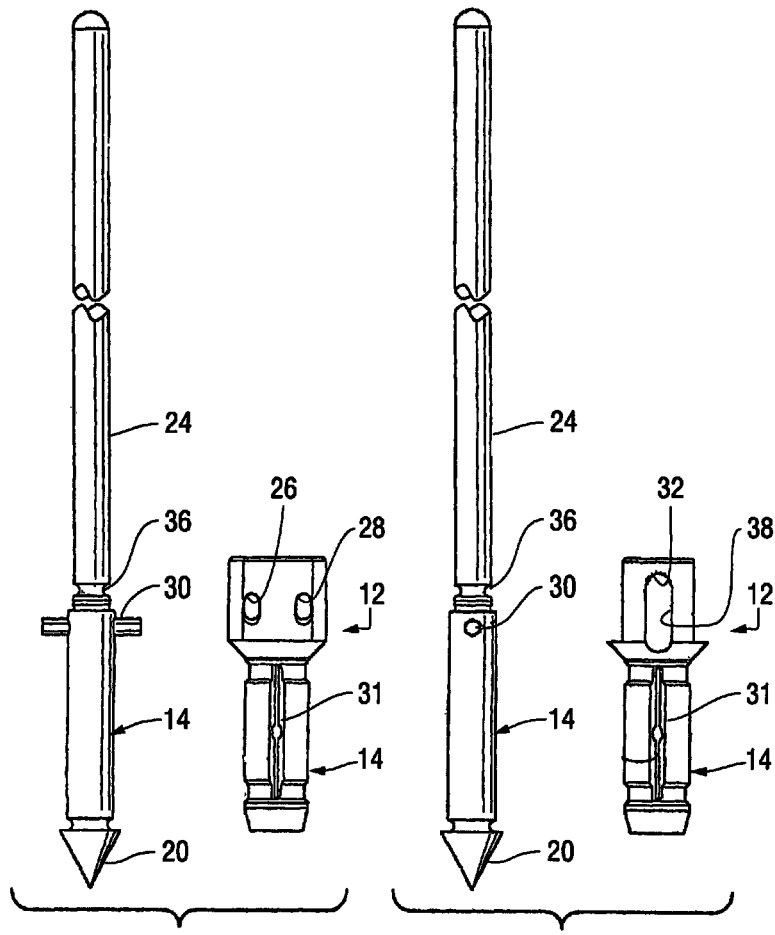
FIG. 3 is a side view in elevation depicting the prior art anchor in its initial condition when attached to the elongated shaft used for inserting the anchor in the bone and a side view in elevation showing one side of the prior art anchor.
FIG. 4 is a view in elevation of the structure depicted in FIG. 3 with each of the components rotated 90 degrees to show the other side view of these structures.

Before the anchor is inserted into the bone the suture 40 is threaded through the soft tissue and looped and then one end is threaded through the diametrically opposing holes 26 and the other end of suture 40 is inserted through the diametrically opposed holes 28. When the shaft 24 is being withdrawn it carries the pin 30 (which may be circular or polygonal in cross section) to ride along the guide slots 38 to force the exposed suture portion into the top curved portion 32 where it is squeezed with sufficient force to lock the suture in place without impairing the strength of the suture. It will be appreciated that before the shaft 24 is withdrawn, the surgeon will grasp the reaches 40A and 40B of the suture and pull it tight so as to cinch the soft tissue to the bone surface. Once these tasks are completed, the surgeon will operate the insertion gun (not shown) until the shaft 24 will break at its frangible slot 36. The features of the suture locking mechanism 12 and the anchor 14 are seen in FIGS. 3 and 4 where the shaft is shown connected to the anchor and slides relative to the suture locking mechanism. The pin 30 that rides in the opposing grooves 38 serves to bear against the suture portions exposed thereto to squeeze those portions up against the inner wall of the locking mechanism 12 to lock the suture in place.

In accordance with this invention, the receptacle of this invention generally illustrated by reference numeral 44 is shown in FIG. 5 comprising a main body 46 having an upper large diameter portion 48 and smaller diameter lower portion 50 and a transitional tapered portion 52. A helical wound course thread 56 extends from the top surface to the bottom surface of the main body noting that the diameter of the threads is constant through out its extent. The purpose of the different diameters of the main body and the equal diameter of the threads is to obtain the maximum holding surface of the thread 56. A tool receiving slot 58 is formed in the proximal end of the main body 46 and is adapted to accommodate the pin 60 at the distal end of tool 62. Tool 62 is shaped generally like a screw driver with the handle 64 at the proximal end and a reduced diameter shaft 66. an O-ring 67 is carried at the distal end of the shaft 66 downstream of the pin 60 which serves to prevent foreign matter to migrate into the internal longitudinal cavity 70 formed in the main body 46. The internal longitudinal cavity 70 is a central bore with a larger diameter 72 at the proximal end, a reduced diameter 74 intermediate the ends of the main body 46, then a larger diameter 76 extending a predetermined longitudinal length, to be described hereinbelow and then a small diameter portion 78 extending to the bottom of main body 46.

In fact, all the dimensions of the internal cavity 70 of main body are critical. The inner diameter is designed to accommodate the tool 62 such that the O-ring 67 extends to the side wall of this cavity to seal the inner portion of the internal cavity while the tool is engaging the slots 58 of the receptacle 44. The diameter of cavity 74 is sufficient to allow the anchor 14 to pass therethrough and enter the recess 76 and the diameter of recess 78 is sufficient to accommodate the tip of the anchor.

Figure 9:
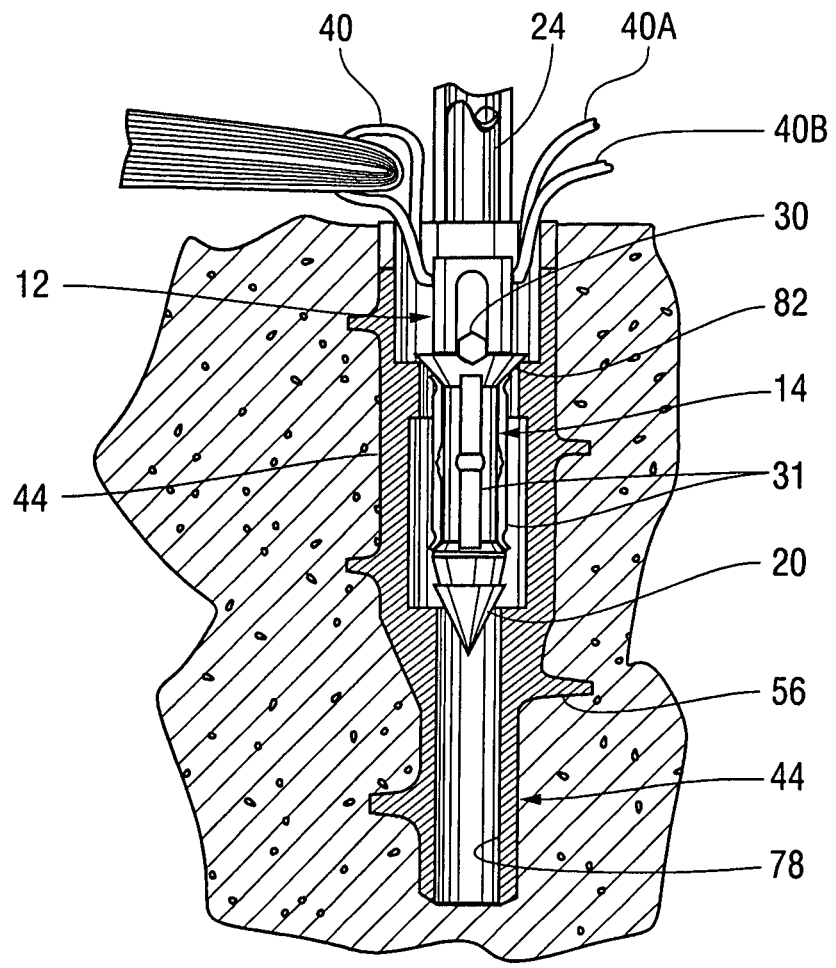
FIG. 9 is a view in schematic and full in schematic illustrating the anchor and the receptical of this invention inserted into the bone.
Figure 10:
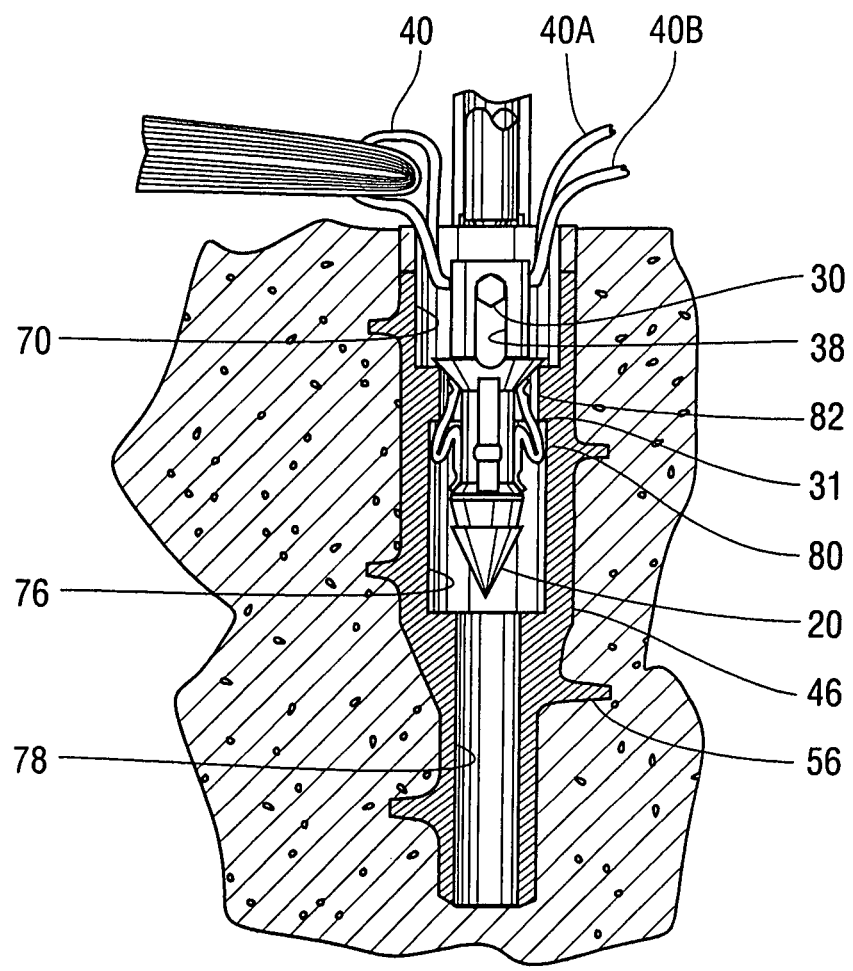
FIG. 10 is a view when the anchor is withdrawn and the wings engage the side wall surfaces of the receptical and the wings tips are folded over.

FIG. 9 illustrates the anchor/suture locking mechanism inserted into the receptacle 44 and the suture looped around the soft tissue before the shaft 24 is severed. FIG. 10 illustrates the mechanism when the anchor is deployed it being noted that the method of inserting the anchor into the receptacle and/or into the bone is substantially the same. Noting that the ends 80 of the wings 31 are configured so that instead of retaining its intended design is now folded over itself. This feature is obtained by making the diameter of the cavity 76 a predetermined dimension and the length of cavity 76 a certain dimension. It also will be noted that the smaller diameter 74 defines the flange or projection 82 that is of a predetermined dimension so as to prevent the anchor from avulsion from the receptacle 44.

Figure 11:
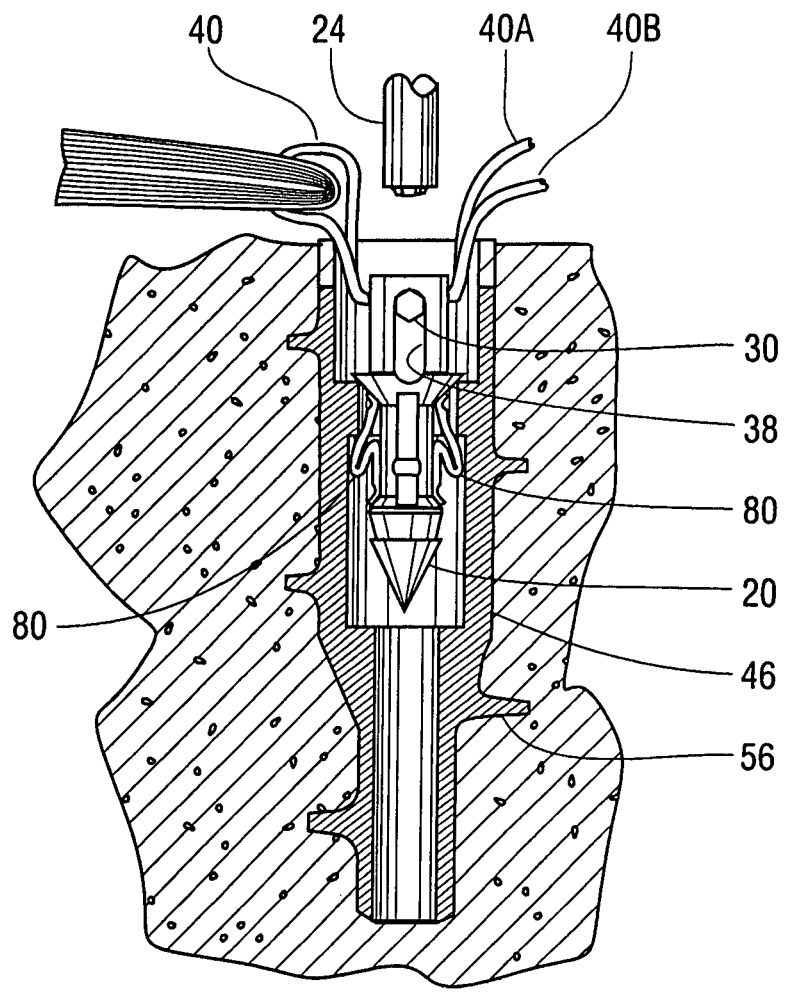
FIG. 11 is a view identical to the structure depicted in FIG. 10 where the shaft is severed at its frangible location.

FIG. 11 depicts the anchor/suture locking mechanism when the shaft 24 is severed. It being noted that the suture 40 is retained by the pin 30 that rides upwardly in the grooves 38 so as to press the suture against the inner upper surface of the locking mechanism 12.

Figure 12:
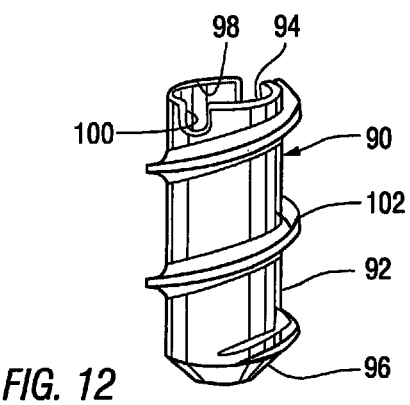
FIG. 12 illustrates another embodiment of this invention and is a perspective view of the receptacle of this invention.
Figure 13:
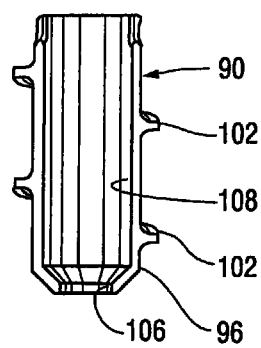
FIG. 13 is a sectional view of the receptacle depicted in FIG. 12.
Figure 14:
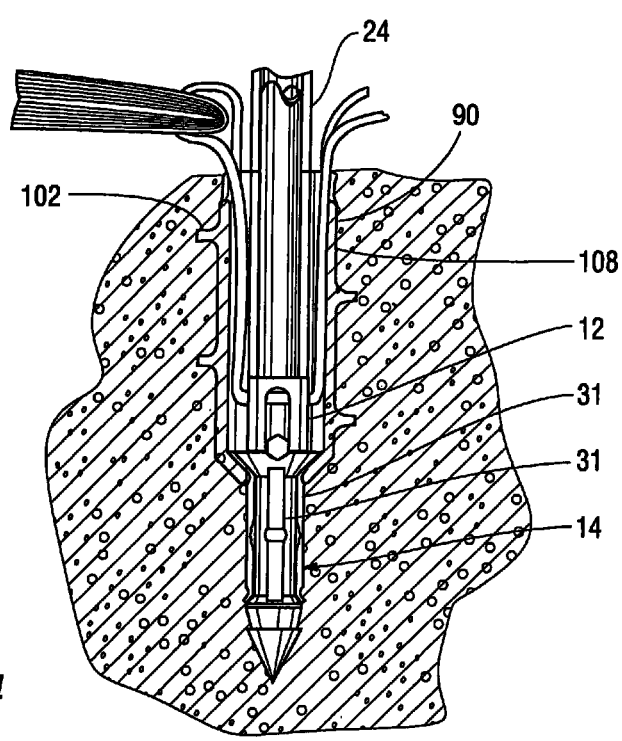
FIG. 14 is a view in section and schematic illustrating the receptacle depicted in FIG. 12 being as utilized for tying a tissue to bone before the anchor is deployed.

FIGS. 12, 13, 14 and 15 exemplify another embodiment of this invention. In this design, both the anchor 14 and the receptacle 90 serve to contact the bone so that the locking of the mechanism is supported by both members. As shown in FIG. 12 the receptacle 90 comprises a main hollowed cylindrical body 92 having a proximal end 94 and a distal end 96. the proximal end includes the inlet portion 98 and opposing slots 100 adapted to receive an insertion tool for screwing the receptacle 90 into the bone. A helix thread 102 is formed on the outer surface of the main body 92 and serves to lock the receptacle to the bone.

The distal end 96 is flared inwardly to provide a reduced diameter end 106 (FIG. 13) which will be described in detail herein below. Similar to the receptacle of the other embodiment the anchor 14 and locking mechanism 12 of the same design, are inserted into the hollow portion 108 which is dimensioned to provide the dual locking characteristics as described above. In this embodiment the diameter of the anchor 14 is smaller than the diameter of the opening 106 and the diameter of the locking mechanism is smaller than the diameter of the hollow portion 108, but is larger than the diameter of the opening 106. Hence, when the combined anchor/locking mechanism is inserted into the receptacle 90 the anchor protrudes beyond the distal end 96 and enters into the bone.

Figure 15:
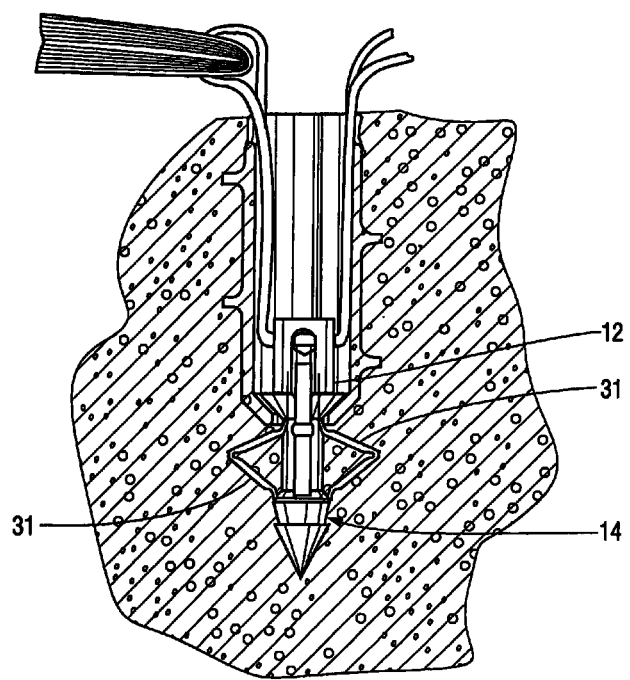
FIG. 15 is a view in section depicting the embodiment in FIG. 14 when the anchor is deployed.

As shown in FIG. 15, when the anchor 14 is deployed, the wings are collapsed so that they extend radially and extend into the bone and the locking mechanism 12 remains above the reduced diameter portion 106 and is deployed similar to what is shown in FIG. 9, Although this invention has been shown and described with respect to detailed embodiments thereof, it will be appreciated and understood by those skilled in the art that various changes in form and detail thereof may be made without departing from the spirit and scope of the disclosed invention.

We claim:

1. A receptacle for receiving an anchor/locking member adapted to be locked into place within a bone of a patient, the anchor/locking member being capable of use independently for anchoring tendons or ligaments in a patient and a locking portion of said anchor/locking member having passages and a movable pin adjacent to said passages for receiving sutures used to anchor the tendons or ligaments so that deployment of the anchor/locking member causes said pin to move to a position to lock the sutures, said anchor/locking member including an anchor portion having a smaller diameter portion and said locking portion having a larger diameter portion, and said anchor/locking member including deployable collapsible radially extending wings defining a "V"-shape and a tip of each of the wings being at an apex of the "V"-shape, said receptacle comprising:

a main cylindrical hollow body having a large diameter outer portion at a proximal end, a reduced diameter outer portion at a distal end, and a tapered portion located between the large diameter outer portion and the reduced diameter outer portion, the main cylindrical hollow body having a helical wound thread formed on an outer surface thereof, the thread engagable with the bone, the main cylindrical body having a central passage extending therethrough, the central passage including:

a cylindrically-shaped first diameter portion extending from an opening provided at the proximal end of the main cylindrical hollow body, the first diameter portion for receiving said anchor portion, a cylindrically-shaped first reduced diameter portion adjacent to said first diameter portion, said first reduced diameter portion for permitting passage of said anchor portion and restraining said locking portion, a cylindrically-shaped increased diameter portion adjacent to said first reduced diameter portion for receiving said anchor portion and permitting said wings of said anchor to extend radially such that the "V"-shape is disposed within said increased diameter portion, and a cylindrically-shaped second reduced diameter portion adjacent to said increased diameter portion and extending from said increased diameter portion to an opening provided at the distal end of the main cylindrical hollow body, wherein said increased diameter portion has a diameter less than a diameter of said first diameter portion, wherein each of said first and second reduced diameter portions have a diameter less than said increased diameter portion.

2. The receptacle as claimed in claim 1 wherein a diameter of said wings of said anchor portion when deployed is larger than the diameter of said increased diameter portion such that the tips of said wings are forced over itself to bear against an inner wall of said increased diameter portion.

3. The receptacle as claimed in claim 2 wherein said anchor portion includes a conical tip end, and said main cylindrical hollow body including said second reduced diameter portion is for accepting said conical tip.

4. The receptacle as claimed in claim 1 wherein an outer peripheral edge of said helical thread defines a major thread diameter that extends a uniform radial distance relative to a longitudinal axis of the main cylindrical body, whereby a portion of said thread corresponding to said reduced diameter outer portion defines a larger contact area with respect to the bone than a portion of said thread corresponding to said large diameter outer portion.

5. The receptacle as claimed in claim 1 wherein said diameter of said second reduced diameter portion is less than said first reduced diameter portion.

6. The receptacle as claimed in claim 1 wherein said tapered portion is located along the main cylindrical hollow body at a location closer to the distal end than the proximal end.

7. The receptacle as claimed in claim 1 including a slot located at the proximal end of the main cylindrical body portion, the slot extending laterally through the main cylindrical body portion.

8. The receptacle as claim in claim 7 wherein said slot defines a U-shaped channel extending through the main cylindrical hollow body.

9. The receptacle as claimed in claim 1 wherein the distal end has a chamfered edge.

10. The receptacle as claimed in claim 1 wherein the helical wound thread is a course thread.

* * * * *